(12) United States Patent  
Zerr et al.

(10) Patent No.: US 8,007,454 B1  
(45) Date of Patent: Aug. 30, 2011

(54) ANKLE SUPPORT ASSEMBLY AND METHOD OF SUPPORTING AN ANKLE

(75) Inventors: John W. Zerr, Hondo, TX (US); Jimmy H. Cody, Grand Prairie, TX (US)

(73) Assignee: George N. Abdou, Rowlett, TX (US)

( * ) Notice: Subject to any disclaimer, the term of this patent is extended or adjusted under 35 U.S.C. 154(b) by 257 days.

(21) Appl. No.: 12/484,687

(22) Filed: Jun. 15, 2009

Related U.S. Application Data

(60) Provisional application No. 61/073,486, filed on Jun. 18, 2008.

(51) Int. Cl.  
*A61F 5/00* (2006.01)

(52) U.S. Cl. .......................................... 602/23; 602/27

(58) Field of Classification Search .......... 602/5, 23–29, 602/60–61, 63, 65; 128/882; 2/22  
See application file for complete search history.

(56) References Cited

U.S. PATENT DOCUMENTS

| 4,494,534 | A | * | 1/1985 | Hutson | 602/16 |
| 5,139,479 | A | * | 8/1992 | Peters | 602/27 |
| 5,501,659 | A | * | 3/1996 | Morris et al. | 602/27 |
| 5,795,316 | A | * | 8/1998 | Gaylord | 602/27 |
| 6,929,617 | B2 | * | 8/2005 | McCormick et al. | 602/65 |
| 2003/0171706 | A1 | * | 9/2003 | Nelson | 602/65 |

OTHER PUBLICATIONS

Web page from http://www.medicalsourcesllc.com/anklecorner.html?gclid=CPPJp4K2jJsCFRMhnAodX0tPpQ, pp. 1-4. Admitted prior art.  
Web page from http://www.achillesmed.com/aso-ankle-brace.html, p. 1, Jun. 15, 2009.  
Web page from http://www.supportsusa.com/gg/aso-ankle-support.htm, pp. 1-2, Jun. 15, 2009.

* cited by examiner

*Primary Examiner* — Michael A. Brown  
(74) *Attorney, Agent, or Firm* — Grady K. Bergen; Griggs Bergen LLP

(57) ABSTRACT

An ankle support assembly is formed from a flexible wrap body comprising a foot wrap portion and an ankle wrap portion. The wrap body is formed from an elastic material to provide a degree of compression when wrapped around the wearer's foot, ankle and leg. The outer surface of the wrap body is provided with hook and loop fastener material. A closure assembly secures the flexible wrap body about the wearer's foot, ankle and leg. At least one elongated side stay positions along at least one of the medial and lateral side of the ankle and the lower portion of the leg of the wearer. The exterior of the elongated side stay has hook and loop fastener material thereon for releasable engagement with the hook and loop fastener material of the wrap body. A stabilizing body positions along one of the medial and lateral sides of the ankle. A circumferential wrap assembly can be selectively tightened or loosened around the wearer's ankle and lower leg portion.

20 Claims, 9 Drawing Sheets

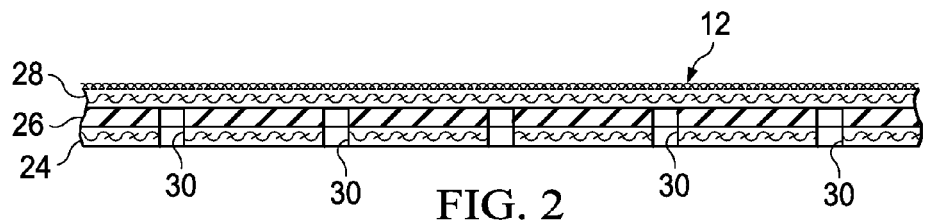
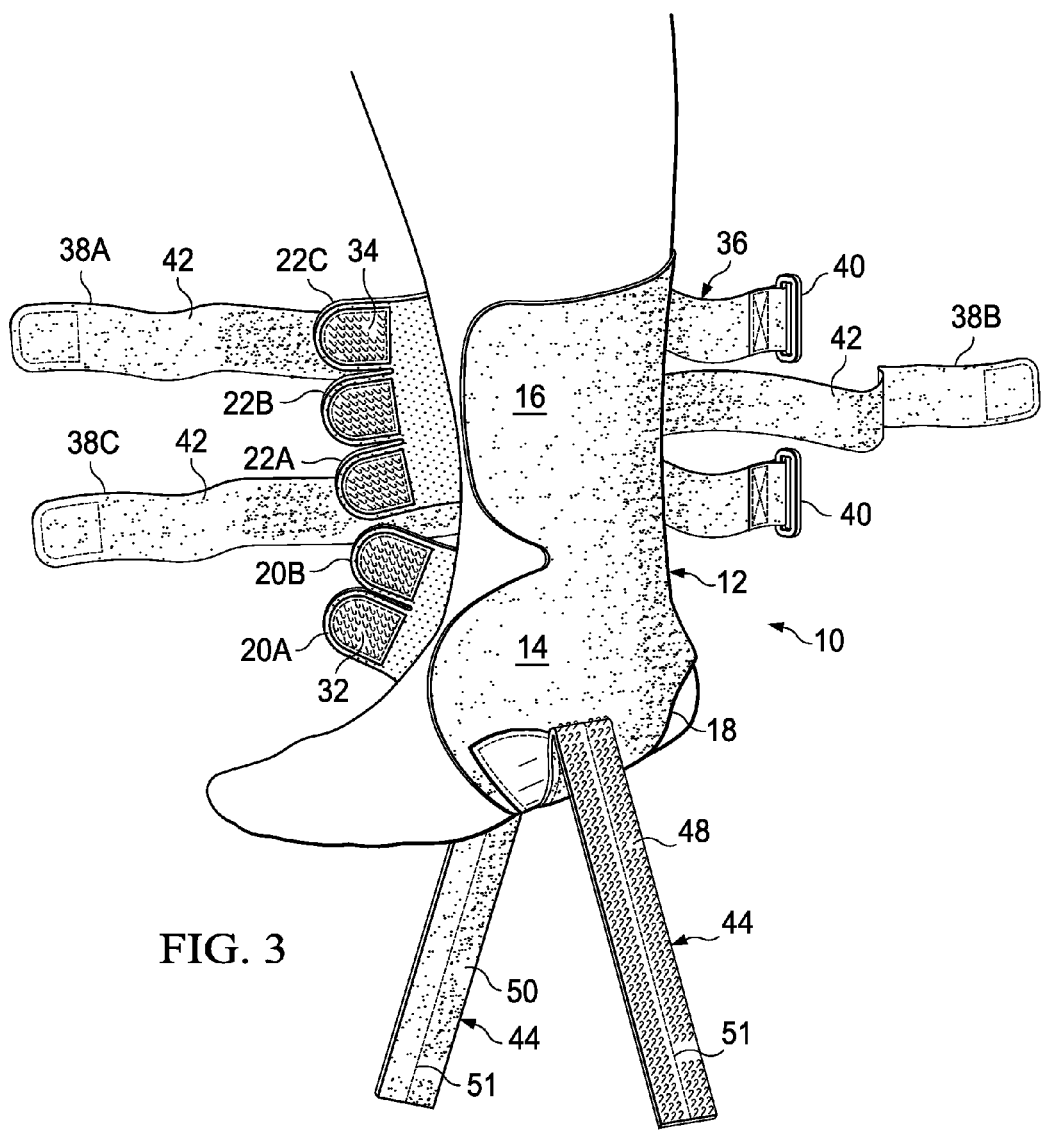

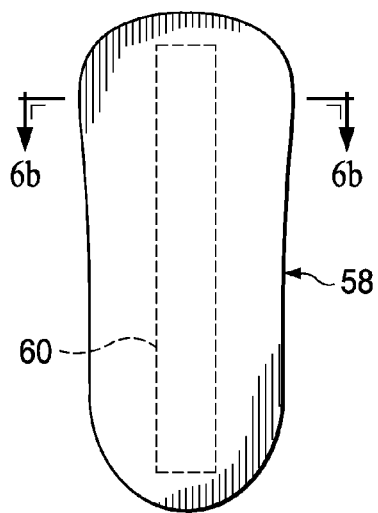
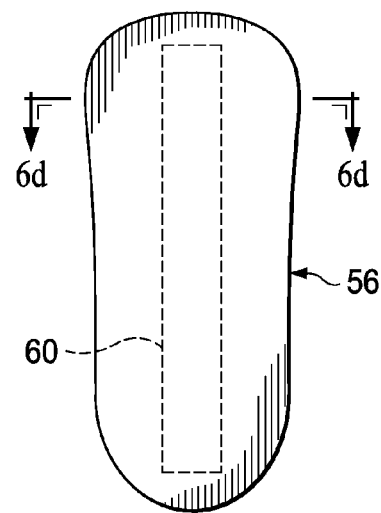
FIG. 6a  FIG. 6c
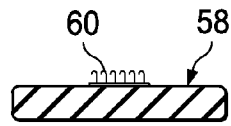
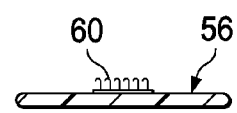
FIG. 6b  FIG. 6d
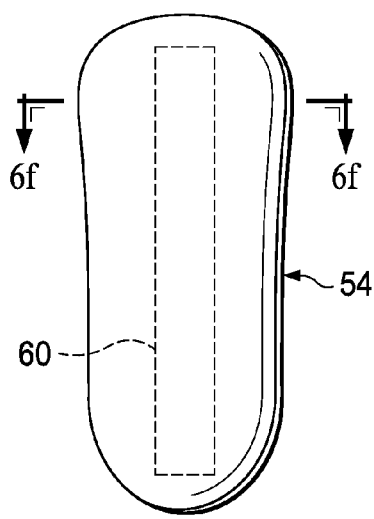
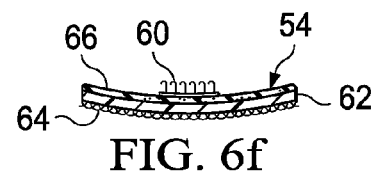
FIG. 6f
FIG. 6e

ANKLE SUPPORT ASSEMBLY AND METHOD OF SUPPORTING AN ANKLE

CROSS-REFERENCE TO RELATED APPLICATIONS

This application claims the benefit of U.S. Provisional Application No. 61/073,486, filed Jun. 18, 2008, which is incorporated herein by reference in its entirety.

BACKGROUND

The present invention relates to devices and methods for stabilizing and supporting an ankle.

BRIEF DESCRIPTION OF THE DRAWINGS

For a more complete understanding of the present invention, and the advantages thereof, reference is now made to the following descriptions taken in conjunction with the accompanying figures, in which:

FIG. 2 is a cross-sectional view of the material forming a wrap body used in forming the ankle support assembly of FIG. 1 taken along the lines 2-2;

FIG. 3 is a side perspective view of the ankle support assembly of FIG. 1 positioned on a wearer's foot prior to closing the ankle support assembly;

FIG. 6a is a top plan view of a first stabilizing body of the ankle support assembly of FIG. 1;

FIG. 6b is a transverse cross-sectional view of the stabilizing body of FIG. 6a taken along the lines 6b-6b;

FIG. 6c is a top plan view of a second stabilizing body of the ankle support assembly of FIG. 1;

FIG. 6d is a transverse cross-sectional view of the stabilizing body of FIG. 6c taken along the lines 6d-6d;

FIG. 6e is a top plan view of a third stabilizing body of the ankle support assembly of FIG. 1;

FIG. 6f is a transverse cross-sectional view of the stabilizing body of FIG. 6e taken along the lines 6f-6f;

DETAILED DESCRIPTION OF THE EMBODIMENTS

Ankle injuries are one of the most common injuries in sports and everyday life. Severe sprains, strains, fractures, and surgeries to the ankle may require protection and immobilization throughout all stages of recovery from post-op through rehabilitation to participation. The present invention combines both immobilization with compression of the lateral joint while allowing for flexion and extension which enables the patient to walk or run. Four different types of stabilizing parts may be utilized to customize all stages of recovery.

Figure 1:
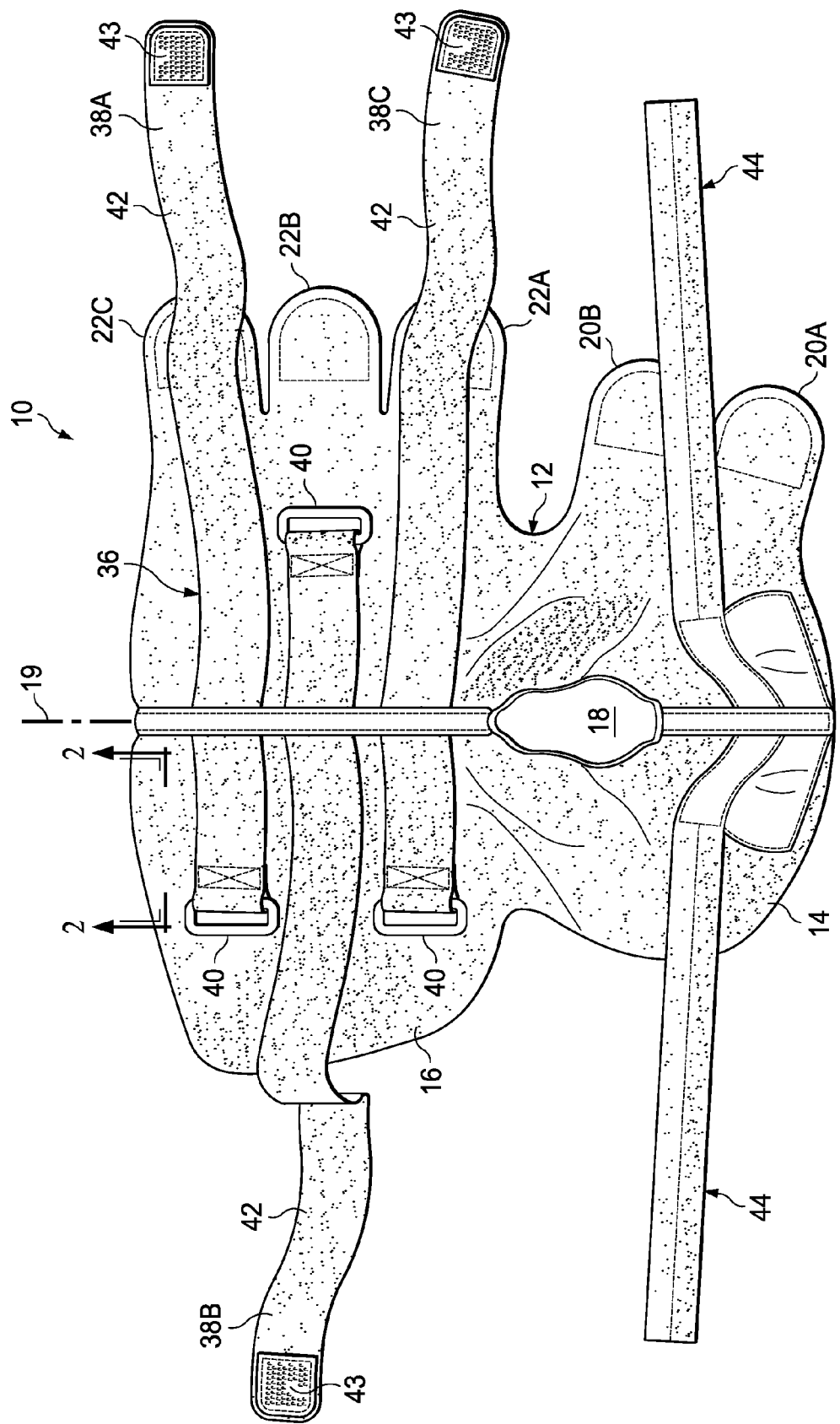
FIG. 1 is a rear elevational view of an ankle support assembly in an open position prior to positioning around a wearer's foot and ankle.

Referring to FIG. 1, an ankle support assembly 10 is shown. The ankle support assembly includes a flexible compression wrap body 12 that is configured for wrapping generally around the mid- and hind-foot portions of a wearer's foot, as well as the wearer's ankle and lower portion of the wearer's leg. As shown, the wrap body 12 may have a general hour-glass shape, with the lower portion 14 forming a foot wrap portion and the upper portion 16 forming an ankle wrap portion, with the neck of the hourglass positioning generally at the bend at the front of the foot. The foot wrap portion 14 may be configured for wrapping generally around the mid- and hind-foot portions of a wearer's foot. The ankle wrap portion 16 is configured for wrapping generally around the wearer's ankle and lower portion of the wearer's leg. The ankle portion 16 may be configured to extend along the wearer's leg above the ankle approximately one third to one half the distance to the wearer's knee to facilitate stabilizing high ankle sprains, which may be from about 5 to about 9 inches above the ankle for most adults. Together, the foot wrap portion 14 and ankle wrap portion 16 of the wrap body 12 is configured to hold the wearer's foot to hold the foot in a 90-degree position relative to the wearer's leg as it wraps the foot, arch, ankle, and the lower position of the tibia/fibula to accommodate high ankle sprains.

An opening 18 may be provided in the wrap body 12 that is configured to receive and accommodate the wearer's heel. The opening 18 may be located generally along a longitudinal centerline 19 that generally bisects the wrap body 12, as shown. The material of the foot portion 14 may be gathered or closed together below the opening 18 along the centerline 19 so that a bend or turn is provided in the wrap body 12 to form the foot portion 14.

A closure assembly formed by closure members or tabs designated generally at 20, 22 provided along one or both side edges of the wrap body 12. The closure members 20A, 20B constitute closure members for the foot wrap portion 14 and the closure members 22A, 22B, 22C constitute closure members for the ankle wrap portion 16. The number of closure members 20, 22 may vary depending upon their size and the size of the foot and ankle portions 14, 16 of the wrap body 12. As an example, there may be from two to four closure members 20 and from two to five closure members 22. The closure members 20, 22 may be formed from extended portions of the wrap body 12 and are configured to overlap the corresponding opposite side edge of the wrap body 12 when it is positioned around the wearer's foot and ankle.

Referring to FIG. 2, a cross section of the material forming the wrap body 12 is shown. As shown, the wrap body 12 is constructed from an inner fabric layer 24. Various materials may be used for the inner layer 24. In most instances, the layer 24 is a soft, natural or synthetic fabric material provided for comfort for interfacing with the wearers foot and ankle. Adjacent to the layer 24 is a layer of an elastic material 26 to provide a degree of compression when the wrap body 12 is wrapped around the wearer's foot, ankle and leg. The layer 26 may be an elastomeric material. In certain embodiments, the elastic layer 26 may be formed from polychloroprene, which is commonly sold under the name NEOPRENE™, or similar elastomer materials, such as elastane or spandex.

The elastic layer 26 is sandwiched between the layer 24 and an outer layer 28. The outer layer 28 may also be a fabric material. All or a portion of the outer surface of the outer layer 28 of the wrap body 12 is provided with hook and loop fastener material (e.g. VELCRO®). In certain embodiments and in the embodiment shown, the outer surface of layer 28 is provided with loop fabric material. It should be noted at the outset that throughout this description where the use of the expression "hook and loop fastener material" or similar expressions are used it may be construed as being either hook material or loop material that is configured for engagement with the other. Thus, if one component of the assembly 10 is described as having hook and loop fastener material that engages the hook and loop fastener material of another component, it should be construed that one component is provided with one of the hook and loop materials and the other material is provided with the other of the hook and loop materials to provide such engagement.

As can be seen in FIG. 2, small holes or apertures 30 may be formed in the layer 26 and may also be formed in the layers 24 and 28, if desired. The holes 30 may be formed to allow air and moisture vapor to pass through the wrap body 12 when non-breathable fabric or material is used. In many cases, the elastic layer will be non-breathable, such as when NEOPRENE materials are used. The holes 30 are sufficient in number and spaced apart and sized to allow air and moisture to pass through the wrap body 12 to facilitate comfort of the wearer. A suitable size for the holes is from less than 1/16 inch to 1/4 inch or more in diameter. As shown in FIG. 2, the holes 30 are formed in both the inner layer 24 and elastic layer 26 but not through the outer layer 28. This is due to the breathability of the outer layer 28. In other embodiments, the materials/layers of the wrap body 12 may not be provided with any holes or apertures and may be formed from breathable or non-breathable materials.

Referring to FIG. 3, the inner face of each of the closure members 20, 22 is provided with a hook and loop fastener material 32, 34, respectively, that is configured for engaging the hook and loop fastener material of the outer layer 28 of the wrap body 12. In the embodiment shown, the hook and loop fastener material 32, 34 is hook material.

Provided with the assembly 10 is a circumferential wrap assembly 36. In the embodiment shown, the wrap assembly 36 is formed by three elongated flexible straps or members 38A, 38B, 38C. Although the wrap assembly 36 is shown with three straps, from two to five straps or more may be used. In some embodiments, a single circumferential strap may be used, although to provide a customized fit of the assembly 10, two or more straps 38 may be preferred. In the embodiment shown, the straps 38 are generally flat lengths of webbing material and are longitudinally spaced apart and coupled to the ankle portion 16 of the wrap body 12 generally along the centerline 19. Coupling of the straps 38 to the wrap body 12 may be facilitated by stitching or other suitable fastening means known in the art. In other embodiments, the straps 38 may be separate or detached from the wrap body 12.

Each of the straps or members 38 may be provided at one end with a buckle or loop 40, which may be formed from metal, rigid plastic or other material. The outer surface of the straps 38 is provided with a hook and loop material 42 generally along their entire lengths. In the embodiment shown, the material 42 is a loop fabric material. On the outer surface at the end of each strap 38 opposite the buckle 40 is provided a short section of hook and loop material 43 configured for engagement with the hook and loop material 42. In this particular embodiment, the material 43 is a hook material.

The inner surface of the straps 38 may be free of hook and loop material, or may be provided with a hook and loop material configured for engagement with the outer surface of the wrap body 12.

As shown in FIG. 1, the orientation of each of the straps 38A, 38B, and 38C is varied so that the buckles 40 of the uppermost and lowermost straps 38A, 38C is on one side of the centerline 19 and the buckle 40 of the center strap 38B is located on the opposite side of the centerline 19. This may help prevent any rotation of the wrap body 10 in any particular direction about the ankle and leg, as the straps are tightened in different directions. As can be seen in FIG. 1, the end of the straps 38 with the buckles 40 are located near the centerline (e.g. from one to three inches) so that the buckles 38 are located generally along the back or side of the assembly 10 when worn.

A pair of elongated side stays 44 are provided with the assembly 10. The side stays 44 may be non-releasably coupled at their lower ends to the bottom of the foot portion 14 of the wrap body 12, such as by stitching or other fastening means. In the embodiment shown, the side stays 44 are coupled at their lower ends to the wrap body 12 generally along the centerline 19.

Figure 4:
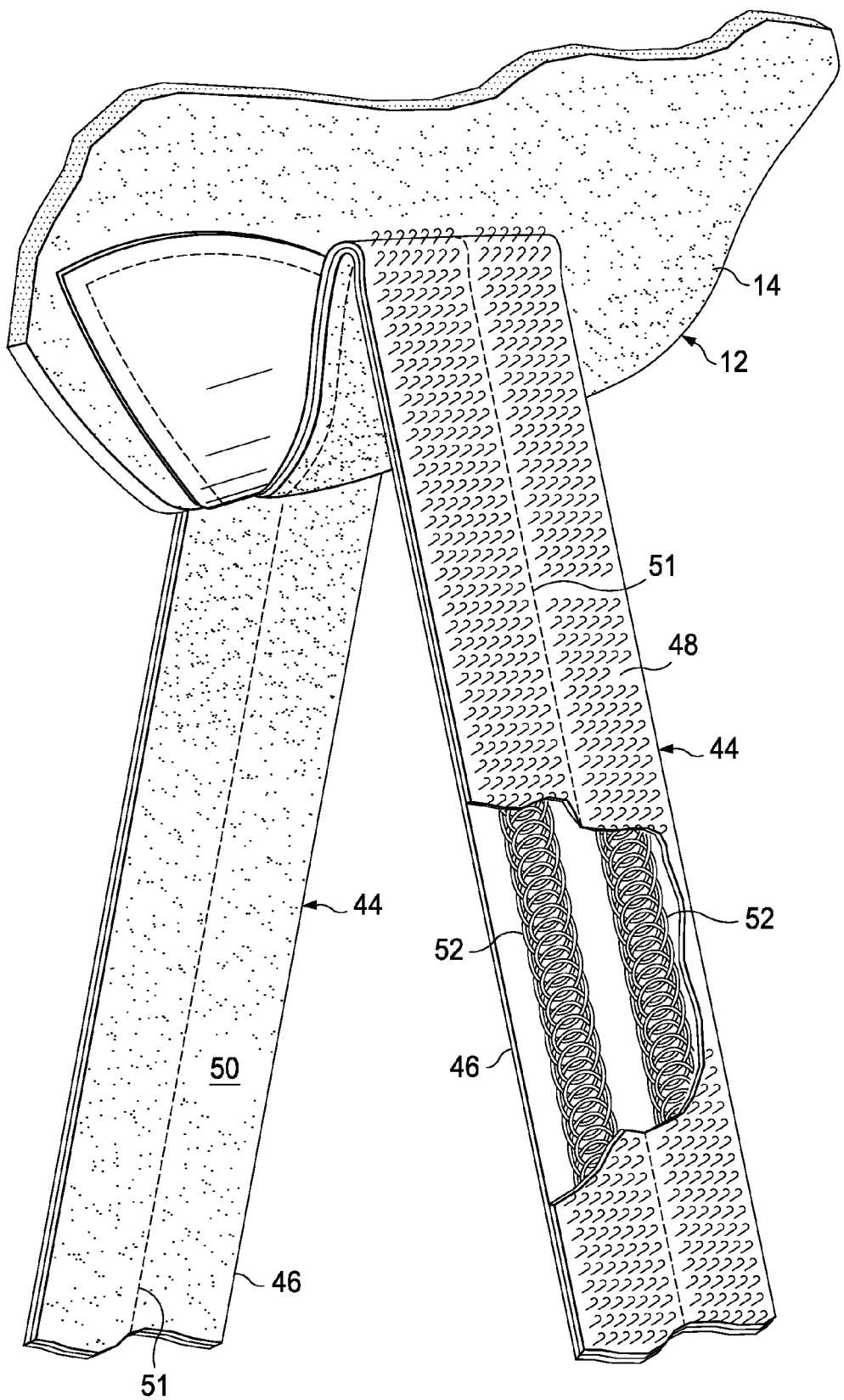
FIG. 4 is an enlarged view of elongated medial and lateral side stays of the assembly of FIG. 1.

As shown in FIG. 4, each of the side stays 44 may be formed from a hollow sleeve 46 of fabric materials. The sleeve 46 may be formed as one piece that wraps below the foot, such as a stirrup, or as two pieces that may each be applied separately. Each side of the sleeve 46 may be provided with different hook and loop materials for releasably coupling to components of the assembly 10. Thus, the inner side 48 of the stay sleeve 46 may have a hook and loop material configured for releasable engaging the hook and loop material of the outer surface of the wrap body 12 or other components. In the embodiment shown, the inner side 48 is provided with hook material. The outer side 50 of the stay sleeve 46 is provided with loop fabric material.

In the embodiment shown, a longitudinal seam 51 is provided down the center of each sleeve 46 to provide a pair of longitudinal pockets. A stay member 52 is received within each pocket of the sleeve 46. The stay members 52 may be flexible or non-flexible. One or more stay members 52 may be provided in each sleeve 46. In certain embodiments, the stay members 52 are semi-rigid, having a degree of flexibility to accommodate movement or bending, but also a degree of stiffness to facilitate supporting of the ankle. In the embodiment shown, the stay members 52 are formed from spiral steel boning material that may be covered at the ends with a plastic coating or end caps to cover of any exposed sharp wire ends that might project through or damage the material of the sleeve 46. The stay members 52 may be formed from other materials, as well, such as plastic, fiberglass, etc., having a sufficient degree of flexibility and stiffness to facilitate flexible support of the ankle.

Figure 5:
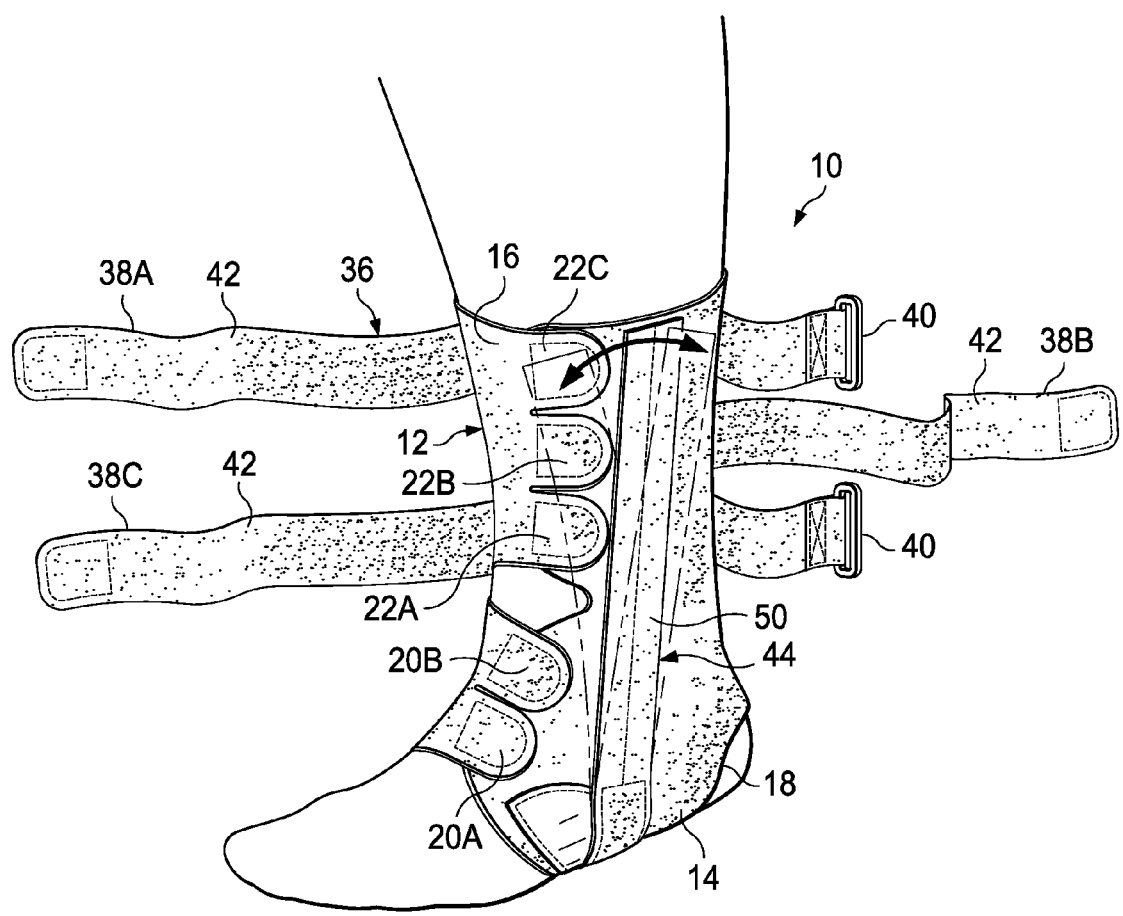
FIG. 5 is a side perspective view of the ankle support assembly of FIG. 1, shown with the ankle support closed and with the side stays being engaged with the wrap body.

As shown in FIG. 5, the side stays 44 may each be applied along the medial and lateral sides of the ankle at various positions, as indicated by the arrows and hidden line outlines. The hook and loop material on the inner side 48 facilitates releasable coupling of the stays 44 to the exterior of the ankle portion 16 of the wrap body 12 so that they stay in the desired position. The side stays 44 may extend substantially the length of the ankle portion 16 but terminate just below the upper end of the ankle portion 16 of the wrap body 12 so that they do not jut out above the wrap body 12. The width of the side stays 44 may be from approximately 1/2 inch to 2 inches or 3 inches.

Referring to FIG. 6, a set of three interchangeable stabilizing bodies 54, 56, 58 is shown and provided with the assembly 10. Each of the three stabilizing bodies 54, 56, 58 has different properties and constructions to provide a different degree of support and flexibility. This is so the stabilizing bodies may be used sequentially or at different times in different modes, which may depend upon the ankle condition or the activities engaged in while wearing the assembly 10. It should be noted that although the assembly 10 is shown and described as having a set of three stabilizing bodies, any number of stabilizing bodies may be provided, each having the same or different properties and constructions. As few as one stabilizing body for positioning on one of the medial or lateral sides of the ankle, or two stabilizing bodies may be provided, one for each of the medial and lateral sides of the ankle. In other embodiments, more than three stabilizing bodies (e.g. 4-6) may be provided in a set. A set may include at least two stabilizing bodies that are the same or similar so that a stabilizing body with the same properties and construction may be provided on both the medial and lateral sides of the ankle.

Each stabilizing body 54, 56, 58 has a width that is greater than the width of the elongated side stay 44 and a length that is less than the length of the elongated side stay 44. In certain embodiments, the stabilizing bodies may have a length of from about 4 inches to about 8 inches, with a width of from about 2 to about 4 inches. The upper and lower ends of the bodies 54, 56, 58 may curved or rounded, with the side edges between the ends being strait or curved.

The stabilizing bodies 54, 56, 58 are positioned medially and/or laterally at the ankle overlaying the malleolus. The stabilizing bodies may be secured to the exterior of the side stays 44 using hook and loop fastener material 60, although other fastening means may also be used. The hook and loop fastener material 60 may be secured to the inner face of the stabilizing body 54, 56, 58 either with an adhesive back or other fastening means, such as stitching, etc. In the embodiment shown, the fastener material 60 constitutes hook material. The stabilizing bodies 54, 56, 58 are then secured to the loop material exterior of the stays 44 or the ankle portion 16 of the wrap body 12.

The stabilizing body 54 is constructed of a thermoplastic material that can be heated and molded to configure to the shape of the wearer's ankle to provide a custom fit. As shown in the cross-sectional view of FIG. 6, the body 54 is provided with a rigid thermoplastic layer 62. The thermoplastic layer 62 may be polyvinyl chloride (PVC) or other thermoplastic that can be heated to soften the layer 62 so that it can be molded and shaped to conform to the wearer's ankle. The layer 62 may be any suitable thickness so that it retains its rigidity once it has cooled. An example of a suitable thickness for the layer 62 is from 1/16 inch to about 1/4 inch, although this may vary. The layer 62 may be pre-formed with a non-flat shape so that the inner surface is generally concave, having a generally arcuate transverse cross section along its length, as shown.

An optional outer layer 64 of fabric material may be provided with the body 54 and be coupled to the outer surface of the inner layer 62. In certain embodiments, the fabric layer 64 may include a hook and loop fastener material. The layer 64 may be coupled to the layer 62 with adhesive or other fastening means or laminating techniques.

In inner layer 66 of cushioning material may be coupled to the inner surface of the rigid thermoplastic layer 62. The layer 66 may include a thin layer of foam material (e.g. 1/8 to 1/4 inch). The layer 66 may be coupled to the layer 62 with adhesive or other fastening means or laminating techniques. The fastener material 60 may be applied to the inner surface of the layer 66 or may be incorporated with the layer 66 as part of its construction.

The stabilizing body 56 may be formed from a single, semi-rigid layer of plastic or polymeric material, such as polypropylene or polyethylene, although other materials may be used. The layer forming the body 56 is generally flat when at rest. The layer 56 is not intended to be molded, as is stabilizing body 54. The layer 56 may have a thickness of from 4 mm, 3 mm or less, more particularly from about 1 mm to about 2 mm. The layer forming body 56, however, has a certain degree of flexibility so that it is deforms from flat to a generally arcuate shape when deformed. This provides a degree of flexible support to the ankle that is less than that provided by the rigid stabilizing body 54.

The stabilizing body 58 is formed from a flexible layer of elastomeric material. This may include a foam material, such as closed cell vinyl or similar material that is generally softer and less rigid than the layer 56. The thickness of the layer 58 may range from 2 mm to 10 mm, 15 mm or 20 mm, more particularly from 3 mm to 10 mm.

As used herein, with respect to the stabilizing bodies 54, 56, 58, the terms "rigid," "semi-rigid" and "flexible," as used respectively with regard to each of the layers, is meant to describe their relative flexibility. It should be understood that each of the bodies 56 and 58 may have some degree of both flexibility and rigidity. Although the body 54 is meant to be generally rigid when cooled, it too may have some degree of flexibility if sufficient force is applied to it, although in normal use it would remain substantially rigid.

Figure 7:
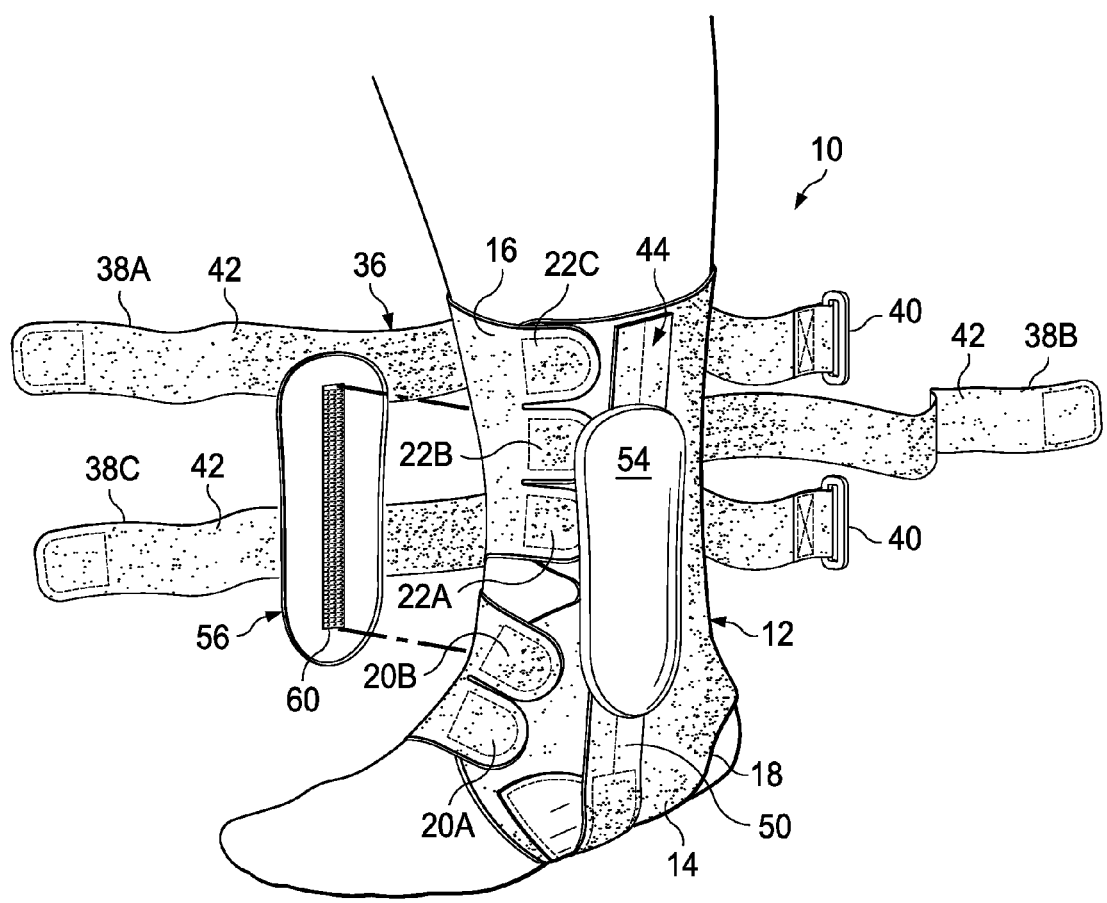
FIG. 7 is a side perspective view of the ankle support assembly of FIG. 1, shown with two stabilizing bodies being positioned over the ankle.

All of the stabilizing bodies 54, 56, 58 may be used medially and laterally, individually or in any combination. As shown in FIG. 7, the stabilizing bodies may be coupled to the medial and lateral sides of the ankle, with the lower end of the stabilizing body extending just below the bottom of the malleolus. The hook and loop fastener material 60 allows the stabilizing bodies to be selectively positioned and repositioned along the sides of the ankle as desired.

Figure 8:
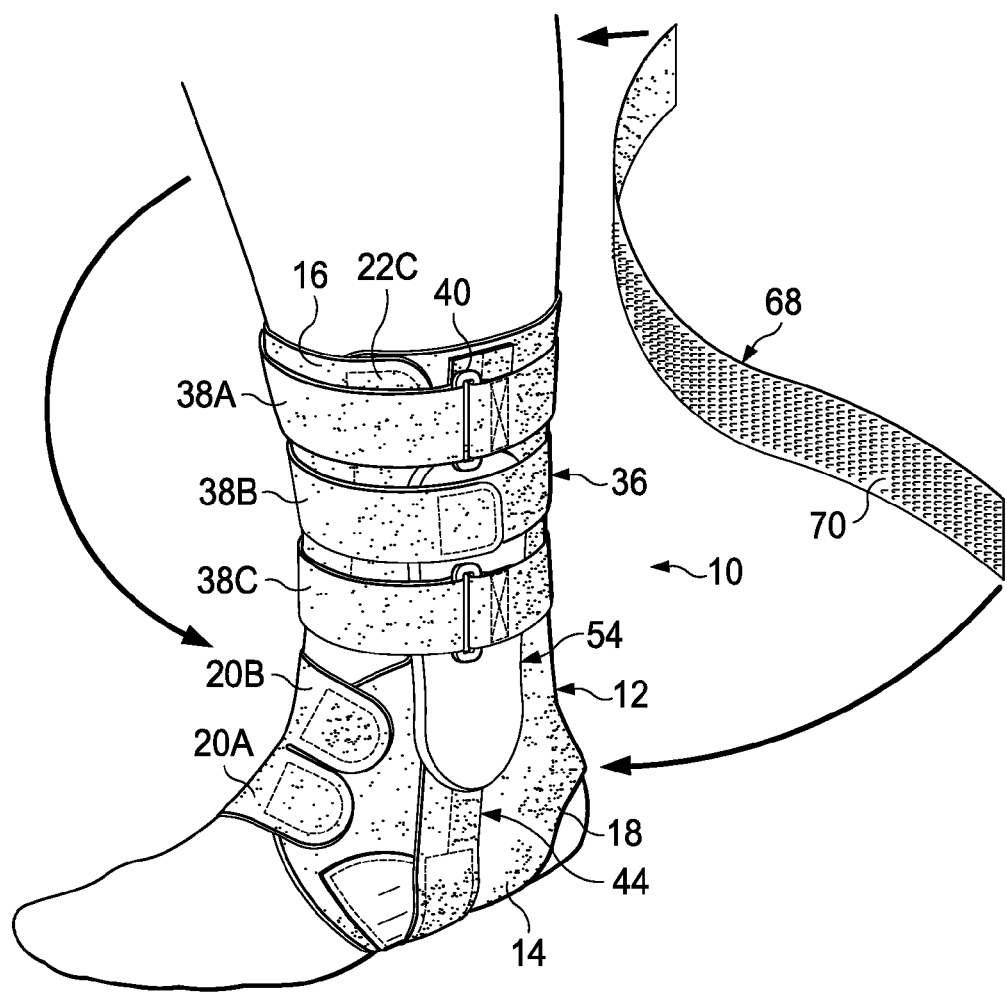
FIG. 8 is a side perspective view of the ankle support assembly of FIG. 1, shown with a circumferential wrap assembly employed.

The stabilizing bodies 54, 56, 58 are further secured by the circumferential wrap assembly 36, as shown in FIG. 8. The circumferential straps 38 wrap around the stabilizing bodies 54, 56 and 58 and the ankle portion 16 of the wrap body 12. The free ends of the straps 38A, 38B, 38C opposite the buckle 40 are looped through the buckle loop of the buckle 40 and back on itself, with the hook material 43 engaging the loop material 42 on the outer surface of each strap 38, so that the end of each strap is attached to itself and is tightly secured around the wearer's ankle and lower leg. This tightly secures the stabilizing bodies 54, 56, 58, the side stays 44 and the ankle portion 16 of the wrap body 12 to the ankle.

Figure 9:
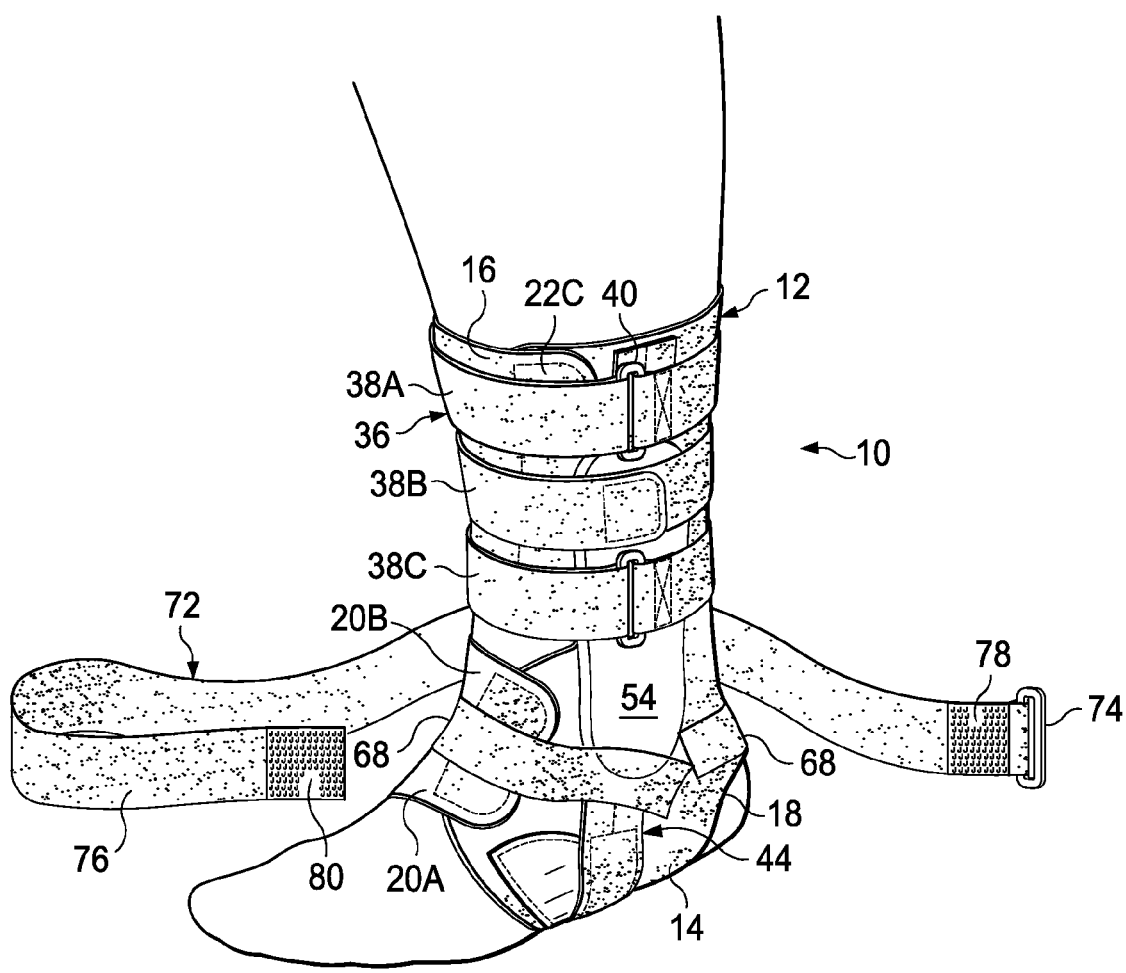
FIG. 9 is a side perspective view of the ankle support assembly of FIG. 1, shown with a flexible heel strap employed.

To further stabilize the ankle, a flexible heel strap 68 may be utilized, as shown in FIG. 8. One side of the flexible strap 68 is provided with hook and loop fastener material 70 to facilitate engagement with the hook and loop material of the wrap body 12. In the embodiment shown, the hook and loop fastener material 70 is hook fastener material. The flexible heel strap 68 is configured to extend from one side of the heel of the wearer around the front of the foot across the top of the wearer's arch to the opposite side of the heel, as shown in FIG. 9. The material 70 facilitates the coupling of the strap 68 to the assembly 10 and across the lower portion of the stabilizing bodies being used. The length of the strap 68 may be adjustable to custom fit each wearer.

A "figure-eight" strap 72 may also used with the assembly 10 to further stabilize the ankle. The strap 72 may be used with or without the heel strap 68. Likewise, the heel strap 68 may be used without the figure-eight strap 72. The figure-eight strap 72 is provided at one end with a buckle 74, which may be in the form of a loop. The outer surface of the strap 72 is provided with hook and loop fastener material 76. In the embodiment shown, the material 76 is loop fastener material. A portion 78 of the inner surface of the strap 72 adjacent to the buckle is also provided with hook and loop fastener material configured to engage the hook and loop material of the wrap body 12. In the embodiment shown, the portion 78 is hook material. A portion of the outer surface of the free end 80 of the strap 72 opposite the buckle 74 is also provided with a hook and loop material configured for engagement with the hook and loop material 76. In the embodiment shown, the free end 80 is provided with hook material.

Figure 10:
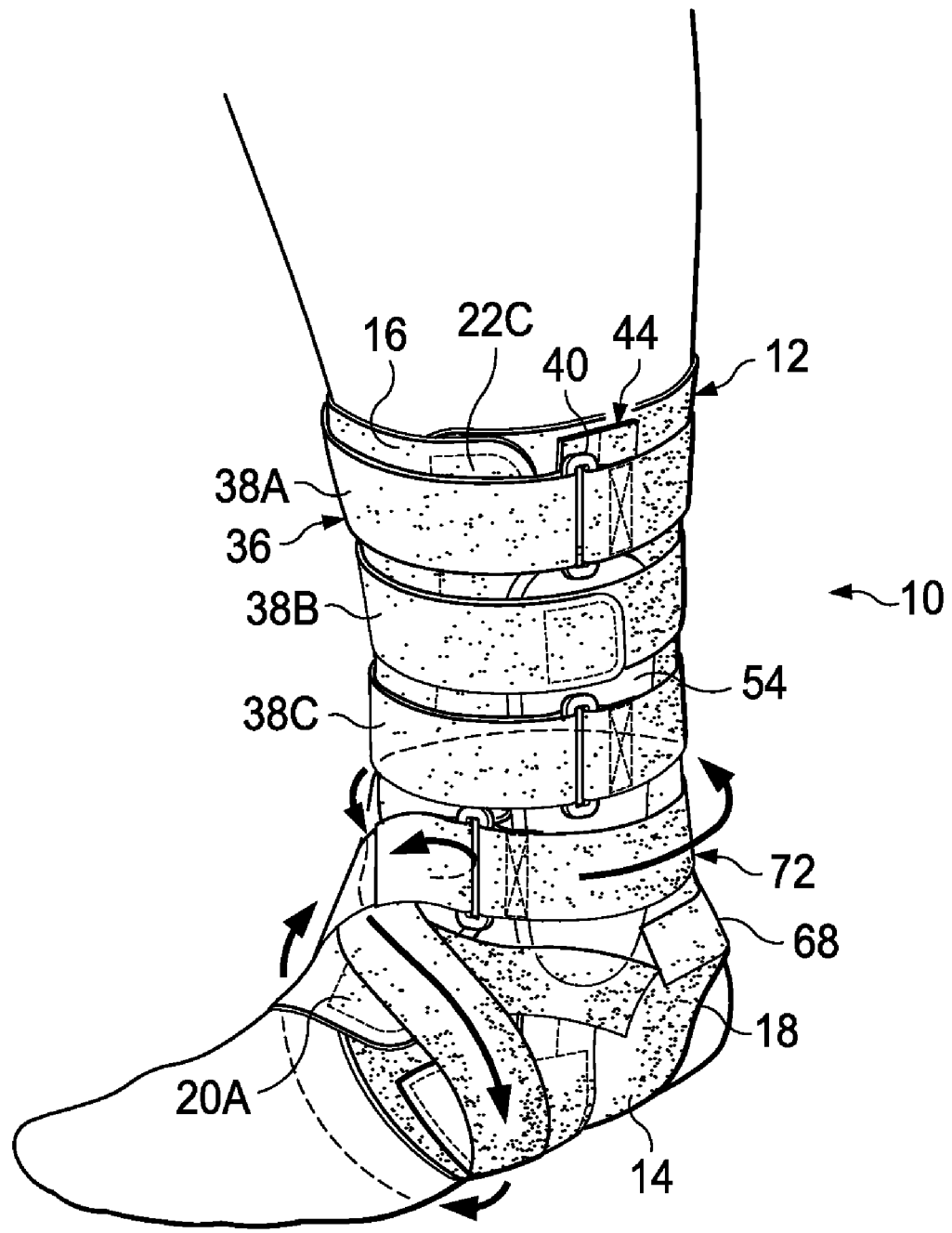
FIG. 10 is a side perspective view of the ankle support assembly of FIG. 1, shown with a flexible figure-eight strap employed.

As shown in FIG. 10, the figure-eight strap 72 loops in a generally figure-eight pattern, with the upper loop 82 wrapping around the stabilizing bodies positioned over the ankle, and the lower loop 84 wrapping around the arch of the foot. To form the figure-eight pattern, the hook material on the inner surface adjacent to the buckle is coupled to the outer surface of the wrap body 12 just forward or behind the stabilizing body positioned on the lateral side of the ankle. The strap 72 is then wrapped behind the leg to the medial side of the ankle and back over the top of the foot to the lateral side of the foot. The strap 72 is then passed under the foot to the medial side and up to and through the buckle 74. The strap is tightened and the free end 80 passing through the buckle 74 is then folded back onto the outer surface of the strap so that the hook material engages and couples to the loop material 76 of the outer surface of the strap 72. It may be necessary to adjust the strap 72 under the foot to be sure it is not twisted or folded so that it is flat against the sole of the foot.

The following describes a method of assembling the ankle support assembly 10 as shown in the drawings. In use, the wrap body 12 is first positioned on the wearer's foot and ankle and snuggly secured utilizing the closure assembly formed by closure tabs 20, 22. In one mode the closure tabs are secured sequentially from bottom to top, with the lowermost closure tabs 20 for the foot being secured first and then the closure tabs 22 for the ankle being closed. In the embodiment shown, the closure tabs are closed in the following order: 20A, 20B, 22A, 22B and 22C.

The side stays 44 are then positioned along the medial and lateral sides of the ankle, to the desired position, as shown in FIG. 5. The hook material of the inner side 48 of each stay 44 engages and couples to the loop material of the wrap body 12 so that it remains in position.

Next, one or more stabilizing bodies 54, 56, 58 is positioned on the sides of the ankle of the wearer, as shown in FIG. 7. As shown in FIG. 7, the stabilizing bodies may be coupled to the medial and lateral sides of the ankle, with the lower end of the stabilizing body extending just below the bottom of the malleolus. The hook and loop fastener material 60 allows the stabilizing bodies to be selectively positioned and repositioned along the sides of the ankle as desired. If the rigid, thermoplastic stabilizing body 54 is to be used, it may first be heated so that it is softened. The body 54 is then molded while softened to conform to the ankle of the wearer where it is to be placed.

The stabilizing bodies 54, 56, 58 provide the flexibility and unique feature of immobilizing and providing compression to the ankle joint, including the fibula on a high ankle sprain, during all three stages of recovery. In one mode of operation, the rigid stabilizing body 54 may be used after a severe sprain, surgery or to otherwise secure the joint during the initial stages of recovery. The stabilizing body 54 may be used on the injured side of the ankle, with the semi-rigid body 56 being used on the opposite side of the ankle. This design helps during critical stages and prevents against further injuries in rehabilitation or participation. The rigid body 54 may be reheated and reshaped to continue customizing the fit, such as when swelling subsides.

The semi-rigid stabilizing body 56 may be used in less severe sprains. The semi-rigid stabilizing body 56 may also be used on the injured side of the ankle during the second stage of recovery to provide stability with compression for the joint to help prevent further injury to the joint, with the flexible body 58 being used on the opposite side of the ankle.

The flexible stabilizing body 58 may be used during the activity stage of recovery, allowing movement of the joint while stabilizing the joint and facilitating the prevention of re-injury to the joint.

The three stabilizing bodies 54, 56 and 58 may be used in any combination. the stabilizing bodies, along with compression wrap, offer immobilization, stabilization and compression to the ankle while allowing for flexion and extension enabling the wearer to walk or run. In certain modes of operation, only one stabilizing body may be used at a time or similar stabilizing bodies may be used simultaneously. Thus, two of each of the stabilizing bodies 54, 56 or 58 may be used at the same time. Stabilizing bodies of varying degrees of rigidity or flexibility and thicknesses may be provided with the assembly 10.

Once the stabilizing bodies 54, 56 and 58 are properly positioned, the circumferential wrap assembly 36 is wrapped around the stabilizing bodies 54, 56 and 58 and the ankle portion 16 of the wrap body 12, as shown in FIG. 8. The free ends of the straps 38A, 38B, 38C opposite the buckle 40 are looped through the buckle loop of the buckle 40 and back on itself, with the hook material 43 engaging the loop material 42 on the outer surface of each strap 38 so that the end of each strap is attached to itself and is tightly secured around the wearer's ankle and lower leg. This tightly secures the stabilizing bodies 54, 56, 58, the side stays 44 and the ankle portion 16 of the wrap body 12 to the ankle.

Finally, the heel strap 68 and/or the figure-eight strap 72 may then be secured, as previously described and shown in FIGS. 9 and 10.

While the invention has been shown in only some of its forms, it should be apparent to those skilled in the art that it is not so limited, but is susceptible to various changes and modifications without departing from the scope of the invention. Accordingly, it is appropriate that the appended claims be construed broadly and in a manner consistent with the scope of the invention.

We claim:

1. An ankle support assembly comprising:
   a flexible wrap body comprising a foot wrap portion and an ankle wrap portion, the foot wrap portion configured for wrapping generally around the mid- and hind-foot portions of a wearer's foot, and wherein the ankle wrap portion is configured for wrapping generally around the wearer's ankle and lower portion of the wearer's leg, the wrap body being formed from an elastic material to provide a degree of compression when wrapped around the wearer's foot, ankle and leg, the outer surface of the wrap body being provided with hook and loop fastener material;
   a closure assembly to secure the flexible wrap body about the wearer's foot, ankle and leg;
   at least one elongated side stay that selectively positions along at least one of the medial and lateral side of the ankle and the lower portion of the leg of the wearer, the exterior of the elongated side stay having hook and loop fastener material thereon for releasable engagement with the hook and loop fastener material of the wrap body;

a stabilizing body that is selectively positionable along one of the medial and lateral sides of the ankle, the stabilizing body having a width that is greater than the width of the elongated side stay and a length that is less than the length of the elongated side stay; and a circumferential wrap assembly at least a portion of which wraps around the stabilizing body, the elongated side stay and the ankle wrap portion of the flexible wrap body, the circumferential wrap assembly being adjustable so that the circumferential wrap assembly can be selectively tightened or loosened around the wearer's ankle and lower leg portion.

2. The ankle support assembly of claim 1, further comprising:

at least one of:
(1) a flexible heel strap that extends from one side of the heel of the wearer around the front of the foot across the arch of the wearer's foot to the opposite side of the heel and having hook and loop fastener material thereon to facilitate securing the heel strap to the wrap body; and
(2) a flexible figure-eight strap that forms an upper loop portion that wraps around the wearer's ankle and a lower loop portion that wraps around the wearer's foot.

3. The ankle support assembly of claim 1, wherein:
there is a set of at least two stabilizing bodies that are interchangeable and selectively positionable along one of the medial and lateral sides of the ankle, each stabilizing body having a width that is greater than the width of the elongated side stay and a length that is less than the length of the elongated side stay, each of the stabilizing bodies within the set having a different degree of flexibility from the others, each stabilizing body having a hook and loop fastener material thereon for engaging the hook and loop fastener material of one of the wrap body and elongated side stay.

4. The ankle support assembly of claim 1, wherein:
there are two elongated side stays, one for each of the medial and lateral sides of the ankle, the elongated side stays each having upper and lower ends wherein the lower ends are non-releasably coupled to the wrap body and the upper ends of the elongated side stays being free to allow the side stays to be selectively positioned along the medial and lateral sides of the ankle and the lower portion of the leg of the wearer.

5. The ankle support assembly of claim 1, wherein:
the stabilizing body is formed from a thermoplastic material that can softened and molded upon heating to conform to the wearer's ankle to provide a customized fit.

6. The ankle support assembly of claim 1, wherein:
the upper end of the ankle wrap portion extends to approximately the mid-calf of the wearer's leg when the ankle support assembly is worn.

7. The ankle support assembly of claim 1, wherein:
the closure assembly comprises at least one closure member having hook and loop material thereon.

8. The ankle support assembly of claim 1, wherein:
the circumferential wrap assembly comprises at least two flexible circumferential straps, each circumferential strap having hook and loop fastener material to facilitate securing around the wearer's ankle or leg, each circumferential strap being independently adjustable so that each circumferential strap can be selectively tightened or loosened.

9. The ankle support assembly of claim 3, wherein:
there is a set of at least three stabilizing bodies, each of the stabilizing bodies within the set having a different degree of flexibility from the others.

10. The ankle support assembly of claim 1, wherein:
the elongated side stay is semi-rigid.

11. An ankle support assembly comprising:
a flexible wrap body comprising a foot wrap portion and an ankle wrap portion, the foot wrap portion configured for wrapping generally around the mid- and hind-foot portions of a wearer's foot, and wherein the ankle wrap portion is configured for wrapping generally around the wearer's ankle and lower portion of the wearer's leg, the wrap body being formed from an elastic material to provide a degree of compression when wrapped around the wearer's foot, ankle and leg, the outer surface of the wrap body being provided with hook and loop fastener material;

a closure assembly to secure the flexible wrap body about the wearer's foot, ankle and leg, the closure assembly comprising at least one closure member having hook and loop material thereon;

a pair of elongated side stays, one for each of the medial and lateral sides of the ankle, the elongated side stays each having upper and lower ends wherein the lower ends are non-releasably coupled to the wrap body and the upper ends are free to allow the side stays to be selectively positioned along one of the medial and lateral sides of the ankle and the lower portion of the leg of the wearer, the exterior of the elongated side stay having hook and loop fastener material thereon for engaging the hook and loop fastener material of the wrap body to releasably couple the upper ends to the wrap body;

a set of at least two stabilizing bodies that are interchangeable and selectively positionable along one of the medial and lateral sides of the ankle, each stabilizing body having a width that is greater than the width of the elongated side stay and a length that is less than the length of the elongated side stay, each of the stabilizing bodies within the set having a different degree of flexibility from the others, each stabilizing body having a hook and loop fastener material thereon for engaging the hook and loop fastener material of one of the wrap body and elongated side stay;

a circumferential wrap assembly, at least a portion of which wraps around the stabilizing body, the elongated side stay and the ankle wrap portion of the flexible wrap body, the circumferential wrap assembly being adjustable so that the circumferential wrap assembly can be selectively tightened or loosened around the wearer's ankle and lower leg portion; and at least one of:
(1) a flexible heel strap that extends from one side of the heel of the wearer around the front of the foot across the arch of the wearer's foot to the opposite side of the heel and having hook and loop fastener material thereon to facilitate securing the heel strap to the wrap body; and
(2) a flexible figure-eight strap that forms an upper loop portion that wraps around the wearer's ankle and a lower loop portion that wraps around the wearer's foot.

12. The ankle support assembly of claim 11, wherein:
at least one of the stabilizing bodies is formed from a thermoplastic material that can softened and molded upon heating to conform to the wearer's ankle to provide a customized fit.

13. The ankle support assembly of claim 11, wherein:
the upper end of the ankle wrap portion extends to approximately the mid-calf of the wearer's leg when the ankle support assembly is worn.

14. The ankle support assembly of claim 11, wherein:
the closure assembly comprises at least one closure member having hook and loop material thereon.

15. The ankle support assembly of claim 11, wherein:
the circumferential wrap assembly comprises at least two flexible circumferential straps, each circumferential strap having hook and loop fastener material to facilitate securing around the wearer's ankle or leg, each circumferential strap being independently adjustable so that each circumferential strap can be selectively tightened or loosened.

16. The ankle support assembly of claim 11, wherein:
there are a plurality of closure members.

17. The ankle support assembly of claim 11, wherein:
there is a set of at least three stabilizing bodies, each of the stabilizing bodies within the set having a different degree of flexibility from the others.

18. The ankle support of claim 17, wherein:
one of the stabilizing bodies is formed from a thermoplastic polyvinyl chloride (PVC) material that can softened and molded upon heating to conform to the wearer's ankle to provide a customized fit and wherein the polyvinyl chloride material is substantially rigid upon cooling, one of the stabilizing bodies is formed from a semi-rigid layer of plastic material having a thicknesss of about 4 mm or less, and one of the stabilizing bodies is formed from a flexible layer of elastomeric material having a thickness of from about 3 mm to about 20 mm.

19. The ankle support assembly of claim 11, wherein:
the elongated side stays are semi-rigid.

20. A method of supporting or stabilizing an ankle of a human comprising:
positioning a flexible wrap body on a wearer's foot and ankle by wrapping a foot wrap portion of the wrap body generally around the mid- and hind-foot portions of a wearer's foot, and wrapping an ankle wrap portion of the wrap body generally around the wearer's ankle and lower portion of the wearer's leg, the wrap body being formed from an elastic material to provide a degree of compression when wrapped around the wearer's foot, ankle and leg, the outer surface of the wrap body being provided with hook and loop fastener material;
securing the flexible wrap body about the wearer's foot, ankle and leg with a closure assembly;
positioning at least one elongated side stay at a selected position along at least one of the medial and lateral side of the ankle and the lower portion of the leg of the wearer, the exterior of the elongated side stay having hook and loop fastener material thereon for engaging the hook and loop fastener material of the wrap body;
positioning a stabilizing body along one of the medial and lateral sides of the ankle, the stabilizing body having a width that is greater than the width of the elongated side stay and a length that is less than the length of the elongated side stay, the stabilizing body having a hook and loop fastener material thereon for engaging the hook and loop fastener materials of one of the wrap body and elongated side stay; and
wrapping a circumferential wrap assembly around the wearer's ankle and lower leg portion so that at least a portion of the circumferential wrap assembly is wrapped around the stabilizing body, the elongated side stay and the ankle wrap portion of the flexible wrap body.

\* \* \* \* \*